(12) United States Patent
Uematsu et al.

(10) Patent No.: US 9,315,931 B2
(45) Date of Patent: Apr. 19, 2016

(54) PRODUCTION PROCESS OF A NONWOVEN FABRIC SHEET

(71) Applicant: UNICHARM CORPORATION, Ehime (JP)

(72) Inventors: Katsuhiro Uematsu, Kagawa (JP); Toru Oba, Kagawa (JP); Satoshi Mizutani, Kagawa (JP)

(73) Assignee: Unicharm Corporation, Ehime (JP)

( * ) Notice: Subject to any disclaimer, the term of this patent is extended or adjusted under 35 U.S.C. 154(b) by 147 days.

(21) Appl. No.: 14/193,904

(22) Filed: Feb. 28, 2014

(65) Prior Publication Data

US 2014/0174628 A1    Jun. 26, 2014

Related U.S. Application Data

(62) Division of application No. 13/637,889, filed as application No. PCT/JP2011/057511 on Mar. 22, 2011, now abandoned.

(30) Foreign Application Priority Data

Mar. 29, 2010   (JP) .................................. 2010-075976

(51) Int. Cl.
*B29C 61/02*    (2006.01)
*B32B 3/30*    (2006.01)
(Continued)

(52) U.S. Cl.
CPC ........ *D04H 13/007* (2013.01); *A61F 13/15699* (2013.01); *A61F 13/51104* (2013.01); (Continued)

(58) Field of Classification Search
CPC ............ A61F 13/15699; A61F 13/511; A61F 13/512; A61F 13/535; A61F 2013/15829; A61F 2013/15878; A61F 2013/15991; A61F 2013/51178; A61F 2013/530145; A61F 2013/530167; A61F 2013/53345; B29C 61/02; B32B 3/30; D04H 1/4382; D04H 1/4391; D04H 1/482; D04H 1/485; D04H 1/49; D04H 1/495; D04H 1/54; D04H 1/541; D04H 1/74; D04H 13/00; D04H 13/003; D04H 13/007

See application file for complete search history.

(56) References Cited

U.S. PATENT DOCUMENTS 3,180,775 A * 4/1965 Sexsmith ............... D04H 1/642
                                                                156/182
3,214,323 A * 10/1965 Russell ..................... D04H 1/66
                                                                156/291

(Continued)

FOREIGN PATENT DOCUMENTS

EP    2 537 969 A1    12/2012
JP    10-502000    2/1998

(Continued)

OTHER PUBLICATIONS

International Search Report based on PCT application No. PCT/JP2011/057511 dated Apr. 14, 2011 (1 pg).

*Primary Examiner* — Michael Tolin
(74) *Attorney, Agent, or Firm* — Brinks Gilson & Lione

(57) ABSTRACT

A sheet of nonwoven fabric which has surface irregularities, the shape of the surface irregularities being less apt to be changed by external pressure, etc. The sheet has a machine, cross and thickness directions which are perpendicular to one another. The upper surface has a plurality of protrusions continuously extending, in parallel, in the cross direction and further has a plurality of recesses that are located between the adjacent protrusions and extend in the cross direction. The sheet includes first and second fibrous layers located on the upper-surface side and the lower-surface side, respectively. The first fibrous layer comprises heat-fusible fibers, and the second fibrous layer comprises coil-shaped three-dimensional crimp fibers that are oriented mainly in the machine direction and form a network by entanglement thereof without having been fused at the sites where the crimp fibers cross one another.

20 Claims, 10 Drawing Sheets

(51) Int. Cl.
*D04H 1/482* (2012.01)
*D04H 1/485* (2012.01)
*D04H 1/49* (2012.01)
*D04H 1/54* (2012.01)
*D04H 1/74* (2006.01)
*D04H 13/00* (2006.01)
*D04H 1/4382* (2012.01)
*D04H 1/541* (2012.01)
*A61F 13/511* (2006.01)
*D04H 1/4391* (2012.01)
*D04H 1/46* (2012.01)
*A61F 13/15* (2006.01)

(52) U.S. Cl.
CPC . *B29C61/02* (2013.01); *B32B 3/30* (2013.01); *D04H 1/4382* (2013.01); *D04H 1/4391* (2013.01); *D04H 1/46* (2013.01); *D04H 1/482* (2013.01); *D04H 1/485* (2013.01); *D04H 1/49* (2013.01); *D04H 1/54* (2013.01); *D04H 1/541* (2013.01); *D04H 1/74* (2013.01); *A61F 2013/15829* (2013.01); *A61F 2013/15878* (2013.01); *A61F 2013/15991* (2013.01); *Y10T 156/1043* (2015.01); *Y10T 428/2457* (2015.01); *Y10T 428/24331* (2015.01)

(56) References Cited

U.S. PATENT DOCUMENTS

| | | | |
|---|---|---|---|
| 5,618,610 A * | 4/1997 | Tomita | D04H 13/003 28/104 |
| 6,171,682 B1 | 1/2001 | Raidel et al. | |
| 6,888,046 B2 * | 5/2005 | Toyoshima | A61F 13/511 604/378 |
| 7,867,348 B2 * | 1/2011 | Uematsu | A61F 13/53713 156/84 |
| 7,955,455 B2 * | 6/2011 | Hanson | B32B 3/28 156/206 |
| 2001/0029141 A1 | 10/2001 | Mizutani et al. | |
| 2003/0203162 A1 * | 10/2003 | Fenwick | A61F 13/15707 428/156 |
| 2008/0044628 A1 | 2/2008 | Noda et al. | |
| 2010/0191207 A1 | 7/2010 | Oba et al. | |

FOREIGN PATENT DOCUMENTS

| | | |
|---|---|---|
| JP | 2001-3281991 | 11/2001 |
| JP | 2008-25082 | 2/2008 |
| JP | 2009-185408 | 8/2009 |
| WO | WO 2009-001590 A1 | 12/2008 |

* cited by examiner

Fig. 6
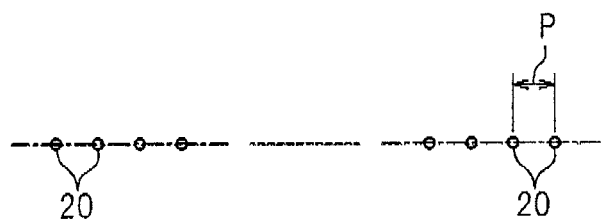
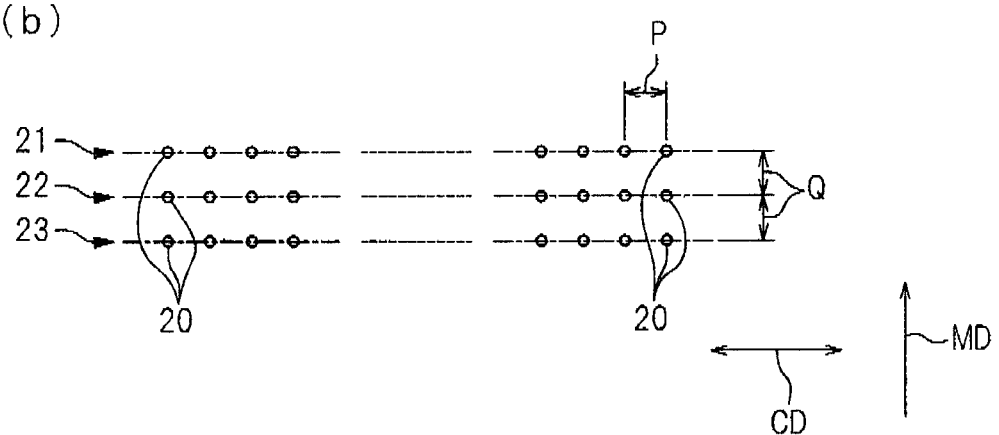
Fig. 7
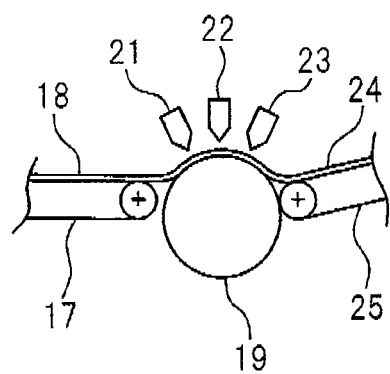

PRODUCTION PROCESS OF A NONWOVEN FABRIC SHEET

RELATED APPLICATION

This application is a divisional application of, and claims priority under 35 U.S.C. §120 to, U.S. patent application Ser. No. 13/637,889, filed Sep. 27, 2012, now abandoned, which is a 35 U.S.C. §371 national phase filing of International Patent Application No. PCT/JP2011/057511, filed Mar. 22, 2011, through which and to which priority is claimed under 35 U.S.C. §119 to Japanese Patent Application No. 2010-075976, filed Mar. 29, 2010.

TECHNICAL FIELD

The present invention relates to a non-woven fabric sheet, a production process thereof, and an absorbent article. In particular, the present invention relates a non-woven fabric sheet in which surface irregularities are formed that is used a surface sheet or absorbent body of a disposable diaper and the like, wherein the surface irregularities are resistant to deformation by external pressure and the like, a production process thereof, and an absorbent article in which the non-woven fabric sheet is provided for use as a surface sheet or absorbent article.

BACKGROUND ART

Japanese Unexamined Patent Publication No. 2008-25082 discloses a process for producing a non-woven fabric, which at least has surface irregularities and allows permeation of a prescribed liquid such as body waste, by emitting air from an upper side onto a fiber web supported from a lower side by a prescribed air-permeable support member to move the fibers that compose the fiber web. It is taught therein that, when producing this non-woven fabric on a production line, the non-woven fabric is formed by increasing the content of fibers oriented in a lengthwise (longitudinal) direction (longitudinally oriented fibers) as a method of increasing resistance of the surface irregularities to deformation caused by line tension (Paragraph [0047]).

Japanese Unexamined Patent Publication (Translation of PCT Application) No. H10-502000 discloses an absorbent article provided with a liquid-permeable surface sheet on a skin side of an absorbent layer. A cover layer having corrugations on a support layer is provided in the absorbent article, leakage of body fluid can be prevented by these corrugations, and comfort when wearing is increased by the flexibility of the corrugations.

SUMMARY OF THE INVENTION

Problems to be Solved by the Invention

As a result of increases in line tension resulting from faster speeds employed by non-woven fabric production lines in recent years, tension is constantly applied to the non-woven fabric in the machine direction (lengthwise direction) in order to stabilize the process.

Even if the content of longitudinally oriented fibers is increased as described in Japanese Unexamined Patent Publication No. 2008-25082, since non-woven fabrics consisting mainly of core-sheath type composite fibers (thermoplastic resin) are formed by melting and fixing intersecting points of the fibers, in the case a sheet is stretched as a result of a load being applied in the machine direction MD due to tensile load generated by line tension, since the fiber network does not have strength to recover from the stretched state once it has been stretched, convex portions may end up being deformed due to deformation of formed protrusions in the machine direction MD. Once these convex portions are deformed, problems occur in which the favorable feel during use resulting from the low contact surface area attributable to surface irregularities is impaired, the gaps in concave portions may no longer be able to be maintained in the case excessive body pressure is applied during use, or body fluid may no longer be able to be retained in the concave portions, causing it to spread onto the skin of the user.

The corrugations of the sanitary napkin described in Japanese Unexamined Patent Publication (Translation of PCT Application) No. H10-502000 are hollow. Accordingly, when the cover layer having the corrugations contacts the skin, the corrugations are easily deformed to a flat shape by body pressure of the wearer. In addition, when body pressure changes when the sanitary napkin is worn and pressure acting on the corrugations has decreased, it is difficult for the cover layer to return from the flattened state to its original corrugated shape. As a result, the cover layer is unable to maintain its optimum shape at all times when the sanitary napkin is worn, resulting in the problem of the occurrence of leakage caused by body waste spreading beyond that which is necessary between the absorbent article and the skin.

Means for Solving the Problems

A first subject invention is a non-woven fabric sheet having a mutually perpendicular machine direction MD, cross-machine direction CD and thickness direction TD, an upper surface and a lower surface in the thickness direction TD, a plurality of protrusions continuously extending in parallel in the cross-machine direction CD formed in the upper surface, and a plurality of recesses extending in the cross-machine direction CD between adjacent protrusions formed in the upper surface; wherein, the non-woven fabric sheet is composed of a first fibrous layer on an upper surface side and a second fibrous layer on a lower surface side, the first fibrous layer contains heat-fusible fibers and the second fibrous layer contains coiled, three-dimensional crimped fibers, and the coiled, three-dimensional crimped fibers of the second fibrous layer are mainly oriented in the machine direction MD, and form a network as a result of entanglement thereof without being fused at those sites where the crimped fibers mutually intersect.

Preferably, the heat-fusible fibers of the first fibrous layer are mainly oriented in the machine direction, and are fused at those sites where they mutually intersect.

Preferably, through holes are present at fixed intervals in the recesses, and the recesses are stretched preferentially to the protrusions when the non-woven fabric sheet is stretched in the machine direction.

Preferably, a plurality of grooves continuously extending in parallel in the machine direction are formed in the lower surface of the non-woven fabric sheet, and the through holes are present in the grooves.

A second subject invention is a production process of a non-woven fabric sheet, comprising:

a) a step for opening a fiber assembly containing heat-fusible fibers by passing through a carding machine to form a web containing heat-fusible fibers, b) a step for opening a fiber assembly containing latent crimpable fibers by passing through a carding machine to form a web containing latent crimpable fibers, c) a step for superimposing the web containing heat-fusible fibers and the web containing latent crimpable fibers to form a laminated web, d) a step for generating a difference in shrinkage force in the machine direction in the laminated web by expressing crimping of the latent crimpable fibers during a heat treatment step over a prescribed width in the machine direction, f) a heat treatment step for heating the web to a temperature that is lower than the fusing temperature of the heat-fusible fibers but causes expression of crimping by the latent crimpable fibers using means for lowering resistance to expression of crimping by the latent crimpable fibers, and g) a step for fusing the web obtained in step f at sites where the heat-fusible fibers mutually intersect by heating to a temperature equal to or higher than the fusing temperature of the heat-fusible fibers.

Preferably, step d is a step in which the laminated web is transported by placing on a support, in which liquid passage portions and protruding liquid blocking portions extending in parallel in the cross-machine direction CD alternately repeat in the machine direction MD, while reorienting the fibers by spraying a liquid from a plurality of nozzles arranged in the cross-machine direction.

Preferably, the means for lowering resistance to expression of crimping by the latent crimpable fibers is a method for transporting at a lower transport speed than that of the previous step.

Preferably, the means for lowering resistance to expression of crimping by the latent crimpable fibers is a floating dryer.

Preferably, the process comprises e) a step for transporting the web obtained in step d to step f between step d and step f.

Preferably, the process comprises h) a step for cooling the web obtained in step g after step g.

A third subject invention is an absorbent article in which the non-woven fabric sheet is provided as a surface sheet or absorbent body.

Effects of the Invention

The non-woven fabric sheet of the present invention is resistant to deformation of surface irregularities caused by external pressure and the like.

Since the non-woven fabric sheet of the present invention contains coiled, three-dimensional crimped fibers in a second fibrous layer, even in the case a load acts in the machine direction MD causing the sheet to be stretched, since the coiled, three-dimensional crimped fibers have stretch recovery due to force that returns them to their original shape, the convex shape of the protrusions of the first fibrous layer is resistant to deformation. In addition, since the fibers of the second fibrous layer are mainly oriented in the machine direction perpendicular to a plurality of protrusions continuously extending in parallel in the cross-machine direction CD, the coiled, three-dimensional crimped fibers are able to maximally demonstrate stretch recovery.

In addition, through holes are present in the non-woven fabric sheet of the present invention at constant intervals in a plurality of recesses extending in the cross-machine direction CD. In addition, protrusions extend continuously in the cross-machine direction CD. Due to the presence of these through holes in the recesses, there are fewer intersecting fibers in comparison with the protrusions, thereby making the strength of the recesses relatively weaker than that of the protrusions. Accordingly, in the case a load acts in a direction perpendicular to the plurality of protrusions continuously extending in parallel in the cross-machine direction CD, the plurality of recesses extending in the cross-machine direction between adjacent protrusions are stretched preferentially to the plurality of protrusions continuously extending in parallel in the cross-machine direction CD, thereby making the convex shape of the protrusions less likely to change.

In addition, fibers of the first fibrous layer are oriented in a direction perpendicular to a plurality of protrusions extending in parallel in the cross-machine direction. As a result of the fibers being oriented in a direction perpendicular to the protrusions, fibers within the protrusions easily adopt an "arch structure" that follows the convex shape of the protrusions. Accordingly, in the case compressive stress acts in the thickness direction of the non-woven fabric sheet, compressive stress acting on the protrusions is dispersed, thereby making the convex shape of the protrusions less likely to be deformed.

In addition, when the non-woven fabric sheet of the present invention is used as a portion of a surface sheet for an absorbent article or a liquid retaining material inside an absorbent article, since it is resistant to crushing even when a force acts in the thickness direction, even in cases in which excessive body pressure is applied during the course of use, the specific volume of the protrusions and the gaps of the recesses can be maintained, thereby enabling body fluid to be temporarily retained in the recesses. Accordingly, body waste does not spread to the skin of a user and leakage can be effectively prevented.

The production process of the non-woven fabric sheet of the present invention enables the non-woven fabric sheet to be produced without causing deformation of the convex shape of the protrusions even in cases in which line tension has been increased as a result of increasing the speed of the non-woven fabric production line. Accordingly, a non-woven fabric enabling rapid permeation of body waste can be stably provided.

BRIEF DESCRIPTION OF THE DRAWINGS

FIG. 6 is a drawing showing the arrangement of a plurality of nozzles arranged in a row in the cross-machine direction used in a step d.

FIG. 7 is a drawing showing an example of a step d differing from that of FIG. 4.

EMBODIMENTS OF THE INVENTION

The following provides an explanation of the present invention based on preferred embodiments thereof with reference to the drawings.

Figure 1:
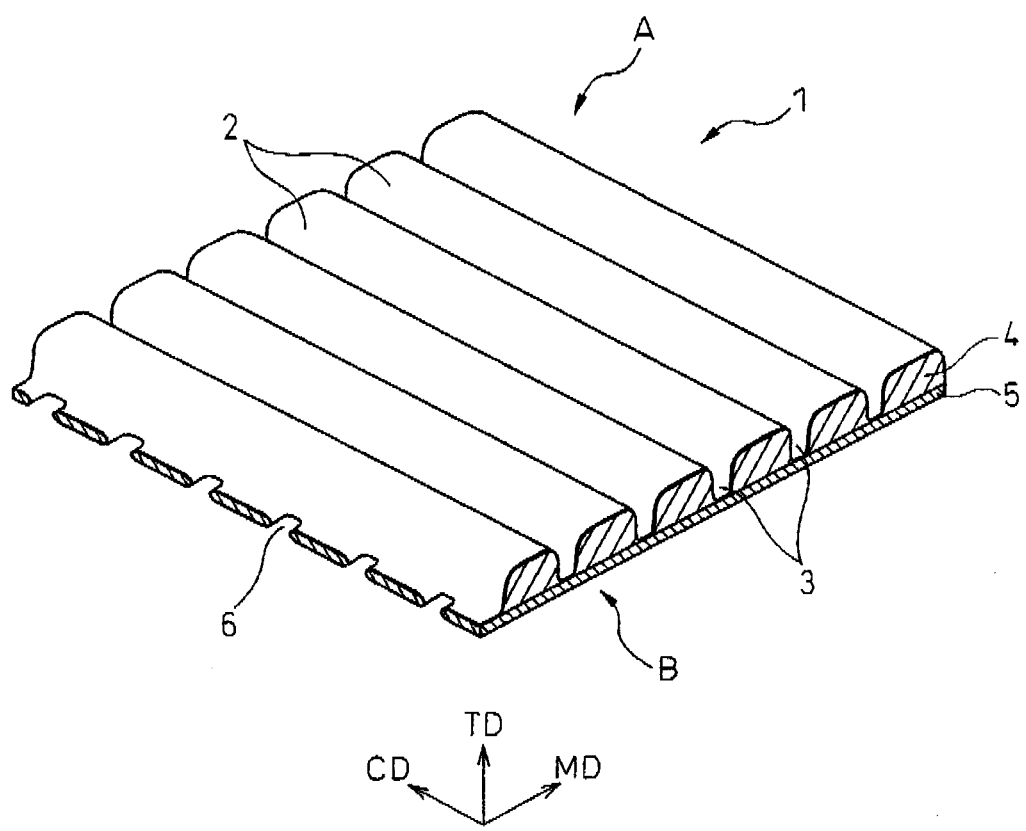
FIG. 1 is a schematic enlarged perspective view showing an embodiment of a non-woven fabric sheet of the present invention.

FIG. 1 is a schematic enlarged perspective view showing an embodiment of a non-woven fabric sheet of the present invention.

A non-woven fabric sheet 1 of the present invention has a mutually perpendicular machine direction MD, a cross-machine direction CD and a thickness direction TD, and an upper surface and lower surface in the thickness direction TD are indicated with reference symbols A and B, respectively. A plurality of protrusions 2 continuously extending in parallel in the cross-machine direction CD, and a plurality of recesses 3 extending in the cross-machine direction CD between adjacent protrusions 2, are formed in the upper surface A.

Figure 2:
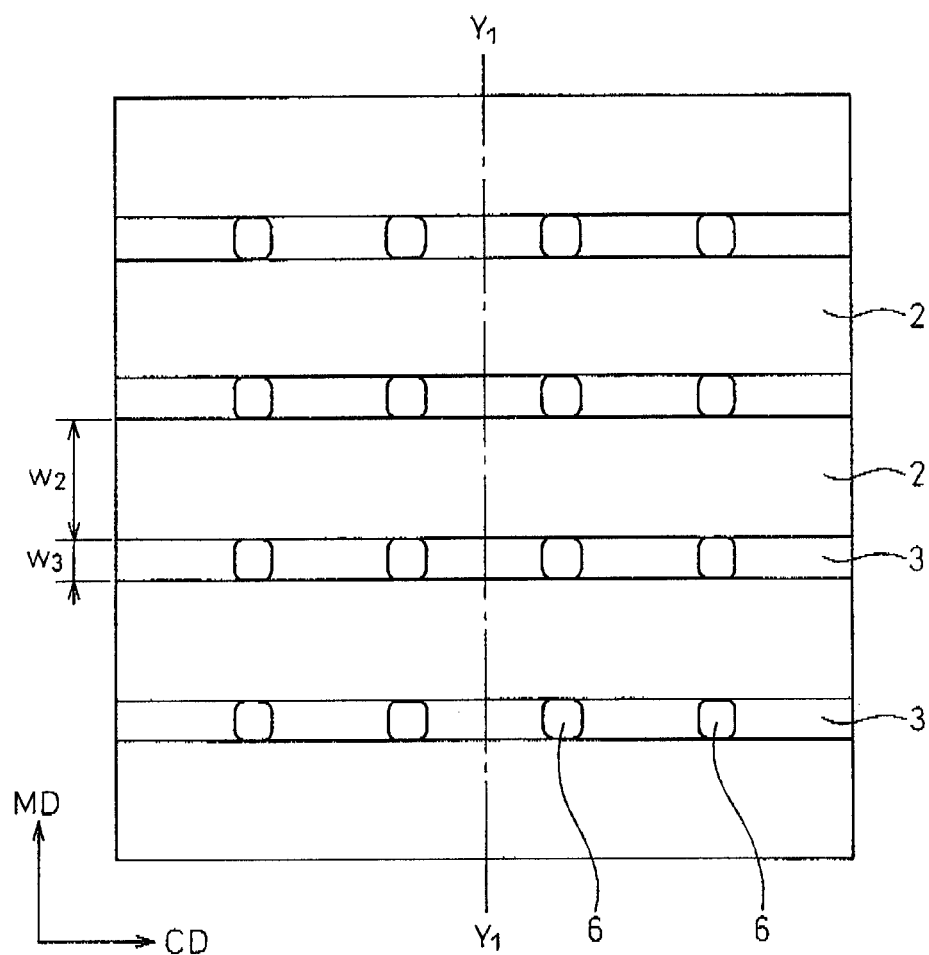
FIG. 2 is a schematic enlarged overhead view showing an embodiment of a non-woven fabric sheet of the present invention.

FIG. 2 is a schematic enlarged overhead view showing an embodiment of a non-woven fabric sheet of the present invention, depicts the non-woven fabric sheet of the present invention as viewed from the upper surface A, and indicates a machine direction MD parallel to the direction of travel of a web on the production line, and a cross-machine direction CD perpendicular to the machine direction MD. The plurality of protrusions 2 extending in parallel to the cross-machine direction and the plurality of recesses 3 extending in the cross-machine direction between adjacent protrusions 2 are formed in the upper surface A.

Figure 3:
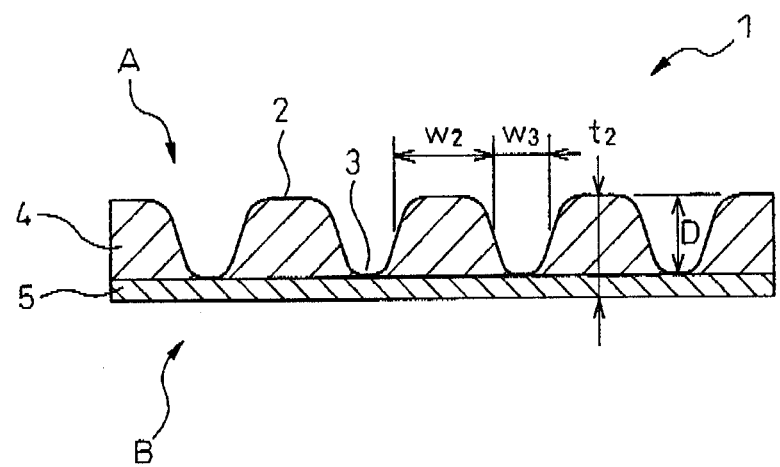
FIG. 3 is a schematic enlarged cross-sectional view taken along line $Y_1$-$Y_1$ of FIG. 2.

FIG. 3 is a schematic cross-sectional view taken along line $Y_1$-$Y_1$ of FIG. 2. The surface used by facing towards the skin of a wearer when the non-woven fabric sheet of the present invention is used as a surface sheet of an absorbent article such as disposable diaper or sanitary napkin is indicated by upper surface A, while the surface on the side of an absorbent body is indicated by the lower surface B. As shown in FIGS. 2 and 3, the non-woven fabric sheet 1 employs a multilayer structure having a first fibrous layer 4 located on the side of the upper surface A and a second fibrous layer 5 located on the side of the lower surface B. The first fibrous layer 4 and the second fibrous layer 5 are integrated into a single unit by a method such as fiber entanglement or heat fusion at the surface where both are opposed.

The second fibrous layer 5 contains coiled three-dimensional crimped fibers in which crimping has been expressed by heating in the production process of the non-woven fabric sheet.

As a result of coiled, three-dimensional crimped fibers being contained in the second fibrous layer, even in the case a load acts on the non-woven fabric sheet 1 in the machine direction and the sheet is stretched, since the second fibrous layer has stretch recovery due a force that causes the coiled, three-dimensional crimped fibers to return to their original shape, the shape of the protrusions of the first fibrous layer is resistant to deformation.

The second fibrous layer 5 has fibers arranged in a direction perpendicular to the plurality of protrusions 2 extending in parallel in the cross-machine direction. Consequently, the force causing the three-dimensional crimped fibers to return to their original shape is demonstrated most easily, and stretch recovery from a load acting in the machine direction MD can be enhanced.

Through holes 6 are present at fixed intervals in the plurality of recesses 3 extending the cross-machine direction CD. In addition, the protrusions 2 extend continuously in the cross-machine direction CD. Since the number of entangled fibers of the recesses 3 is less than that of the protrusions 2 due to the presence of the through holes 6, strength of the recesses 3 is relatively weak in comparison with that of the protrusions 2. Accordingly, in the case a load has acted in the machine direction MD, the plurality of recesses extending in the cross-machine direction between adjacent protrusions are stretched preferentially to the plurality of protrusions extending continuously in parallel in the cross-machine direction CD, thereby resulting in less susceptibility to deformation of the convex shape of the protrusions.

A thickness $t_2$ of the protrusions 2 (see FIG. 3) is preferably 0.3 mm to 5 mm and more preferably 0.5 mm to 3 mm from the viewpoint of ensuring favorable absorbency and texture against the skin of the non-woven fabric sheet 1. If the thickness $t_2$ exceeds these ranges, an awareness of the use of the non-woven fabric sheet 1 on the skin ends up increasing. In addition, if the thickness $t_2$ is below these ranges, the non-woven fabric sheet 1 is more greatly affected by the reduced overall thickness of the non-woven fabric sheet, thereby reducing the rate of liquid permeation.

A height difference D (see FIG. 3) between the top of the protrusion 2 and the bottom of the recesses 3 is preferably 0.1 mm to 5 mm and more preferably 0.3 mm to 3 mm from the viewpoint of forming the recesses 3 to be suitable for making it difficult for a prescribed large amount of liquid to spread out over a wide area of the surface of the non-woven fabric sheet 1 when the liquid has been excreted. In the case of having exceeded these ranges, the height of the protrusions 2 inevitably becomes higher, thereby increasing the awareness of the use of the non-woven fabric sheet 1 on the skin. In addition, in the case of being below these ranges, the amount of a prescribed liquid able to be taken up into the recesses 3 decreases, thereby resulting in increased likelihood of the liquid spreading out over the surface.

A width $w_2$ of the protrusions 2 in the cross-machine direction CD of the non-woven fabric sheet 1 is preferably 1 mm to 10 mm and more preferably 2 mm to 5 min from the viewpoint of absorbency. From the same viewpoint, a width $w_3$ of the recesses 3 in the machine direction of non-woven fabric sheet 1 is preferably 0.5 mm to 7 mm and more preferably 1 mm to 3 mm. Even if a state is employed that prevents the protrusions 2 from being crushed when excessive external force has been applied, the spaces formed by the recesses 3 are easily maintained, making it possible to create less susceptibility to a prescribed liquid oozing out and spreading over a wide area on the surface even if the prescribed liquid is excreted in a state in which external pressure has been applied.

The protrusions 2 and the recesses 3 may be formed to have the same width or may be formed to have different widths. The widths of the protrusions 2 and the recesses 3 can be altered in various ways corresponding to the width in the machine direction MD of projections 45 of a molding plate 41 used in the production process to be subsequently described. For example, the width of the recesses can be reduced by reducing the width in the machine direction MD of the protrusions 45 of the molding plate 41. Conversely, the width of the recesses can be increased by increasing the width in the machine direction MD of the projections 45 of the molding plate 41.

The height of the protrusions 2 can be reduced by reducing the interval at which the projections 45 of the molding plate 41 are attached. Conversely, the height of the protrusions 2 can be increased by increasing the interval at which the projections 45 of the molding plate 41 are attached. Moreover, the protrusions 2 having different heights can be alternately formed by forming such that the intervals at which the projections 45 of the molding plate 41 are attached alternate between a narrow interval and a wide interval. In addition, if the height of the protrusions 2 is partially changed in this manner, there is also the advantage of being able to reduce the load on the skin since contact surface area of the skin decreases.

In addition, the height of the protrusions can also be changed by changing the height of the projections 45 of the molding plate 41. For example, if the height of the projections 45 of the molding plate 41 is decreased, the height of the protrusions also decreases. Conversely, if the height of the projections 45 of the molding plate 41 is increased, the height of the protrusions also increases.

The first fibrous layer 4 is composed of a fibrous layer in which heat-fusible fibers are contained as essential fibers, while the second fibrous layer 5 is composed of a fibrous layer in which latent crimpable fibers are contained as essential fibers.

Heat-fusible fibers are contained as primary fibers in the first fibrous layer 4 as 30% by weight to 100% by weight. The mutually crossing heat-fusible fibers of the first fibrous layer 4 are bound by melting a thermoplastic resin of which they are formed. As a result of the heat-fusible fibers being mixed into the first fibrous layer in the amount indicated above, shape retention of the three-dimensional shape of the concave shape of the protrusions 2 can be enhanced.

Fibers composed of a thermoplastic resin are preferably used for the fibers that enable heat fusion of the intersecting points of the fibers contained in the first fibrous layer 4. Examples of thermoplastic resins include polyolefins such as a polyethylene or polypropylene, polyesters such as polyethylene terephthalate, and polyamides. In addition, core-sheath or sandwich type composite fibers consisting of a combination of these thermoplastic resins can also be used. The fusing temperature of the heat-fusible fibers contained in the first fibrous layer 4 is preferably 10° C. or more higher, and more preferably 30° C. or more higher, than the temperature at which the latent crimpable fibers used in the second fibrous layer 2 begin to crimp. In the case the difference between the fusing temperature of the heat-fusible fibers contained in the first fibrous layer 4 and the temperature at which the latent crimpable fibers used in the second fibrous layer 5 begin to crimp is smaller than the aforementioned ranges, fusion of the heat-fusible fibers contained in the first fibrous layer 4 begins and the heat-fusible fibers end up fusing prior to the demonstration of coiled, three-dimensional crimping by the latent crimpable fibers used in the second fibrous layer 5. Accordingly, the non-woven fabric ends up being formed into a sheet in a state in which the latent crimpable fibers used in the second fibrous layer 5 do not adequately demonstrate coiled, three-dimensional crimping, thereby decreasing stretch recovery from a load acting in the machine direction MD.

The first fibrous layer 4 may be composed of one type or two or more types of fibers enabling heat fusion of the intersecting points of the fibers, or in addition to fibers enabling heat fusion of the intersecting points of the fibers, may also be comprised of these fibers and other fibers that do not undergo heat fusion. For example, one or more types of natural fibers such as wool or synthetic fibers such as polypropylene, polyethylene, polyester, polyamide, polyvinyl chloride or vinylon fibers may be arbitrarily selected and used. In addition, there are no limitations on the cross-sectional shape and so forth of these fibers, and split-type composite fibers or modified cross-section fibers can also be used arbitrarily. In this case, the amount of fibers enabling heat fusion of intersecting points of the fibers is preferably 30% by weight to 95% by weight, and more preferably 70% by weight to 90% by weight, of the weight of the first fibrous layer 4.

From the viewpoint of favorable texture against the skin and absorbency of the non-woven fabric sheet 1, the fineness of fibers used in the first fibrous layer 4 is preferably 1 dtex to 5 dtex and more preferably 1.8 dtex to 3.3 dtex. If fineness ends up exceeding these ranges, discomfort is imparted to the user due to the excessive thickness of the fibers, while if fineness is below these ranges, the distance between fibers becomes excessively short resulting in increased susceptibility to resistance and decreasing the permeation rate of a prescribed liquid. In addition, from the viewpoint of proper carding, the length of the fibers used is preferably 15 mm to 65 mm and more preferably 38 mm to 51 mm.

The heat-fusible fibers that compose the first fibrous layer are preferably mainly oriented in the machine direction MD. Orienting the fibers in the machine direction MD (longitudinal direction) refers to the fibers being oriented within a range of +45 degrees to −45 degrees with respect to the machine direction MD, and fibers oriented in the machine direction refer to longitudinally oriented fibers. Orienting fibers in the cross-machine direction CD (transverse direction) refers to the fibers being aligned within the range of +45 degrees to −45 degrees with respect to the cross-machine direction, and fibers oriented in the cross-machine direction are referred to as transversely oriented fibers. Fibers oriented mainly in the machine direction MD means that the number of fibers oriented in the machine direction MD is greater than the number of fibers oriented in the cross-machine direction. The content of longitudinally oriented fibers in the first fibrous layer is preferably 55% to 100% and more preferably 60% to 100%. As a result of fibers being oriented in a direction perpendicular to the protrusions 2, fibers within the protrusions 2 easily adopt an "arch structure" that follows the convex shape of the protrusions 2. Accordingly, in the case compressive stress has acted in the thickness direction of the non-woven fabric sheet 1, since the compressive stress that acts on the protrusions 2 is dispersed, there is less likelihood of deformation of the convex shape of the protrusions. A web in which fibers are mainly oriented in the machine direction MD can be formed by opening the fibers by passing through a carding machine, and the fibers can be further oriented in the machine direction MD by continuously spraying a liquid onto the web in the machine direction.

Measurement of fiber orientation can be carried out in the manner described below using the VHX-100 Digital Microscope manufactured by Keyence Corp. (1) A sample is placed on an observation stage so that the machine direction MD is the longitudinal direction, (2) the focus of a lens is aligned with the fibers closest to the front of the sample while excluding those fibers irregularly protruding towards the front, and (3) a 3D image of the sample is generated on a PC screen by setting the depth of field (depth). Next, (4) the 3D image is converted to a 2D image, (5) a plurality of parallel lines are drawn on the screen that suitably equally divide the measuring range in the machine direction. (6) Fiber orientation in each of the divided cells formed by drawing the parallel lines is observed to be in the machine direction or cross-machine direction, and the number of fibers oriented in each direction is measured. Finally, (7) the ratio of the number of fibers oriented in the machine direction and the ratio of the number of fibers oriented in the cross-machine direction to the total number of fibers within the set range are calculated.

The second fibrous layer 5 contains crimped fibers that express crimping as a result of being heated in the production process. Crimped fibers that express crimping as a result of being heated in the production process refer to latently crimpable fibers used as a raw materials of the non-woven fabric sheet that express crimping as a result of being heated in the production process of the non-woven fabric sheet. Latently crimpable fibers refer to fibers that express crimping as a result applying heat. Since these fibers are composed of two or more types of fibers having different melting points and their heat shrinkage rates change according to the their difference in melting points when heat is applied, these refer to three-dimensional crimped fibers. Examples of the resin composition of the fiber cross-section include eccentric types having a core-sheath structure and side-by-side types in which the left and right components have different melting points. As a result of latently crimpable fibers being contained in the second fibrous layer in the production process of the non-woven fabric sheet, the entire web shrinks as a result of the latently crimpable fibers of the second fibrous sheet expressing crimping, thereby enabling the formation of protrusions. The crimped fibers are coiled, three-dimensional crimped fibers. Coiled crimped fibers refer to fibers that have been crimped into the shape of a coil. Three-dimensional fibers refer to fibers having a three-dimensional crimped shape in the manner of a coiled shape. As a result of coiled, three-dimensional crimped fibers being contained in the second fibrous layer, even in the case the sheet is subjected to a load and stretched in the machine direction MD, the sheet has stretch recovery due to a force that acts to return the coiled, three-dimensional crimped fibers to return to their original shape, thereby resulting in less susceptibility to deformation of the convex shape of the protrusions of the first fibrous layer. The crimped fibers of the second fibrous layer form a network due to entanglement of the coiled, three-dimensional crimped fibers. In this type of fiber network, since there is no bonding at the intersecting points, even if an external force in the manner of compression is applied thereto, deformation at the intersecting points is unrestricted, and the network is able to easily return to its original shape after deformation due to the action of the coiled, three-dimensional crimped fibers. The formation of a network refers to forming a state in which fibers are mutually linked by entanglement and heat fusion of the fibers.

The crimped fibers are contained in the second fibrous layer 5 at 30% by weight to 100% by weight. Examples of latent crimpable fibers that compose the second fibrous layer 5 include eccentric core-sheath type composite fibers or side-by-side type composite fibers composed of two types of thermoplastic resins having different shrinkage rates. In addition, the area shrinkage rate of the web is preferably at least 40% from the viewpoint of forming protrusions by shrinking the second fibrous layer 5. For example, a combination of polyolefin-polypropylene copolymer and polypropylene can be used. In addition, from the viewpoint of favorable liquid permeability, the fineness of the fibers used is preferably 1 dtex to 11 dtex and more preferably 2.2 dtex to 6.6 dtex. In addition, the length of the fibers used is preferably 15 mm to 65 mm and more preferably 38 to 51 mm from the viewpoint of proper carding.

Furthermore, web area shrinkage rate is measured in the following manner.

(1) A 200 g/m² web is produced with 100% of the fibers to be measured.

(2) The web is cut to a prescribed length and width followed by measurement of area. The web is preferably cut to about 250 mm×250 mm in order to reduce measurement error at this time. The measured area prior to shrinkage is designated as "a".

(3) The cut web is allowed to stand for 5 minutes in an oven controlled to 145° C.

(4) Area is calculated by measuring the length and width after shrinkage. The measured area after shrinkage is designated as "b".

(5) The area shrinkage rate is calculated from the areas before and after shrinkage based on the following equation.

Area shrinkage rate (%)=$(a-b)/a \times 100$

The second fibrous layer 5 may be composed of one type or two or more types of latent crimpable fibers, or may be composed of non-latent crimpable fibers or other fibers that do not heat-fuse with the fibers in addition to the latent crimpable fibers. For example, one or more types of fibers can be arbitrarily selected and use from among regenerated fibers such as rayon fibers, semi-synthetic fibers such as acetate fibers, natural fibers such as cotton or wool fibers, and synthetic fibers such as polypropylene, polyethylene, polyester, polyamide, polyvinyl chloride or vinylon fibers. There are no limitations on the cross-sectional shape and so forth of the fibers used in the second fibrous layer 5, and split-type composite fibers or modified cross-section fibers can be used arbitrarily. The use of modified cross-section fibers having a Y-shaped or cross-shaped cross-section for the second fibrous layer 5 results in the presence of grooves in the fibers and enables capillary force to be increased due to surface contact among the fibers in comparison with fibers having a round cross-section. Accordingly, as a result of the formation of a difference in capillary force between the first fibrous layer 4 and the second fibrous layer 5, liquid that has been incorporated in the first fibrous layer 4 is allowed to easily migrate to the second fibrous layer 5, and in the case of using as a surface sheet or absorbent body of an absorbent article, excreted liquid is able to separate from the skin of a user more rapidly. The blending ratio of the latent crimpable fibers composing the second fibrous layer 5 is preferably 30% by weight or more and more preferably 80% by weight or more from the viewpoint of demonstrating adequate heat shrinkage.

The crimped fibers of the second fibrous layer 5 are not fused at those sites where the crimped fibers mutually intersect. If the crimped fibers are fused at those sites where the crimped fibers mutually intersect, shrinkage behavior of the latent crimpable fibers is inhibited. Thus, fibers allowing heat-fusing of intersecting points of the fibers at a temperature at which the latent crimpable fibers contained in the second fibrous layer 5 express crimping in the second fibrous layer 5 are preferably not contained in the second fibrous layer 5.

The temperature at which the latent crimpable fibers used in the second fibrous layer 5 express crimping is preferably lower than the temperature at which intersecting points of the heat-fusible fibers used in the first fibrous layer 4 are able to heat-fuse. The protrusions 2 can be formed in the first fibrous layer 4 as a result of the second fibrous layer 5 shrinking before the shape of the fibers of the first fibrous layer 4 are fixed by heat fusion. The temperature at which the latent crimpable fibers express crimping is preferably 10° C. or higher and preferably 30° C. or higher than the heat fusing temperature of the heat-fusible fibers contained in the first fibrous layer 4. In the case the difference between the fusing temperature of the heat-fusible fibers contained in the first fibrous layer 4 and the temperature at which the latent crimpable fibers used in the second fibrous layer 5 begin to crimp is smaller than the aforementioned ranges, the fusion of the heat-fusible fibers contained in the first fibrous layer 4 begins and the heat-fusible fibers ends up fusing before the latent crimpable fibers used in the second fibrous layer 5 express coiled, three-dimensional crimping. Accordingly, since a sheet ends up being formed without the latent crimpable fibers used in the second fibrous layer 5 adequately expressing coiled, three-dimensional crimping, stretch recovery in a response to a load acting in the machine direction MD ends up decreasing.

A plurality of grooves continuously extending in parallel in the machine direction MD are preferably formed in the lower surface B of the non-woven fabric sheet of the present invention, and the aforementioned through holes are present in the grooves. In a preferred aspect of a step d to be subsequently described, the grooves are formed in a region subjected to spraying of liquid from a plurality of nozzles arranged in a row in the cross-machine direction. As a result of these grooves being formed, since gaps capable of temporarily retaining a liquid are obtained in the lower surface as well, liquid can be prevented from overflowing back onto the upper surface when under pressure in combination with the effects of the gaps of the recesses. Accordingly, leakage is more effectively prevented without allowing excreted liquid to spread out onto the skin of a user.

The basis weight of the non-woven fabric sheet 1 following the shrinkage step is preferably 25 g/m$^2$ to 400 g/m$^2$ and more preferably 40 g/m$^2$ to 200 g/m$^2$. The basis weight of the first fibrous layer 4 following the shrinkage step is preferably 15 g/m$^2$ to 250 g/m$^2$ and more preferably 25 g/m$^2$ to 180 g/m$^2$, while the basis weight of the second fibrous layer 5 following the shrinkage step is preferably 10 g/m$^2$ to 150 g/m$^2$ and more preferably 15 g/m$^2$ to 120 g/m$^2$.

The non-woven fabric sheet 1 is preferably hydrophilic. The non-woven fabric sheet 1 can be made to be hydrophilic by, for example, using fibers that have been treated with a hydrophilizing agent for the raw material thereof. In addition, a method can also be used in which fibers incorporating a hydrophilizing agent are used for the raw material. Moreover, a method can also be used that uses fibers inherently possessing hydrophilicity, such as natural fibers or semi-natural fibers. The non-woven fabric sheet 1 can also be made to be hydrophilic following the production thereof by coating with a surfactant.

Next, an explanation is provided of a method for producing the non-woven fabric sheet of the present invention.

One embodiment of a method for producing the non-woven fabric sheet of the present invention comprises the following steps; however, steps e and h of the following steps are not required:

a) a step for opening a fiber assembly containing heat-fusible fibers by passing through a carding machine to form a web containing heat-fusible fibers, b) a step for opening a fiber assembly containing latent crimpable fibers by passing through a carding machine to form a web containing latent crimpable fibers, c) a step for superimposing the web containing heat-fusible fibers and the web containing latent crimpable fibers to form a laminated web, d) a step for generating a difference in shrinkage force in the machine direction in the laminated web by expressing crimping of the latent crimpable fibers during a heat treatment step over a prescribed width in the machine direction, e) a step for transporting the web obtained in step d to step f, f) a heat treatment step for heating the web to a temperature that is lower than the fusing temperature of the heat-fusible fibers but causes expression of crimping by the latent crimpable fibers using means for lowering resistance to expression of crimping by the latent crimpable fibers, g) a step for fusing the web obtained in step f at sites where the heat-fusible fibers mutually intersect by heating to a temperature equal to or higher than the fusing temperature of the heat-fusible fibers, and h) a step for cooling the web obtained in step g.

Figure 4:
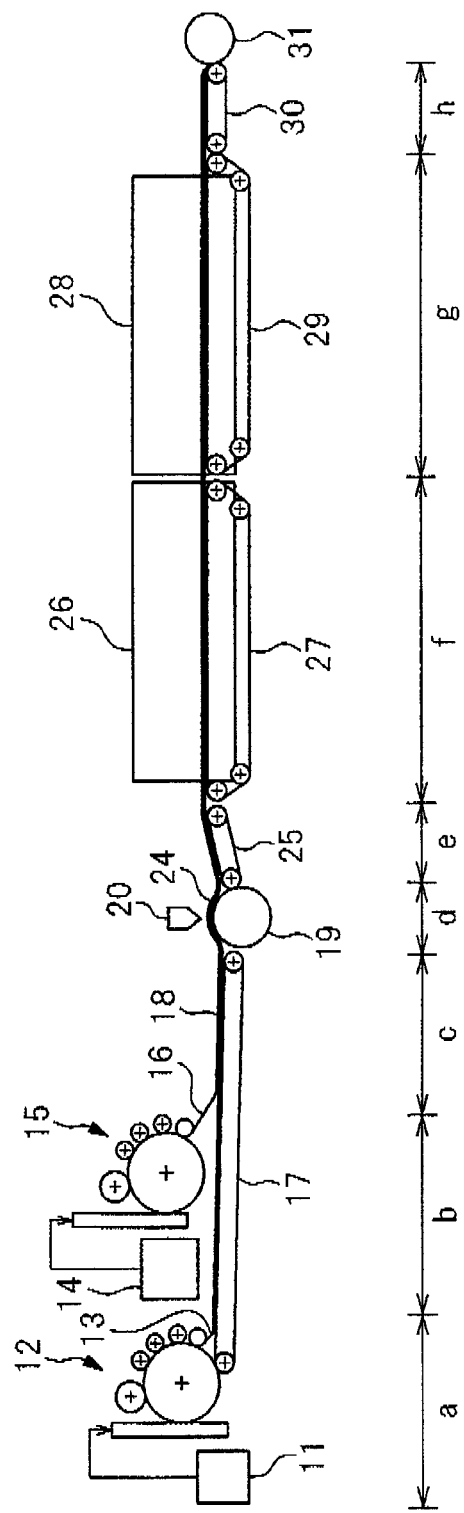
FIG. 4 is a drawing showing an example of the production steps of a non-woven fabric sheet of the present invention.

FIG. 4 shows an example of the production steps of the non-woven fabric sheet of the present invention. However, the present invention is not limited to this example.

In FIG. 4, a indicates step a, b indicates step b, c indicates step c, d indicates step d, e indicates step e, f indicates step f, g indicates step g, and h indicates step h.

In step a, a fiber assembly containing heat-fusible fibers is transported from a container 11 to a carding machine 12, and the assembly is opened by passing through the carding machine 12 to form a web 13 containing heat-fusible fibers. The formed web 13 containing heat-fusible fibers is transported by placing on an endless belt 17. As a result being opened by passing through the carding machine, the fibers can be made to be mainly oriented in the machine direction MD. The basis weight of the formed web 13 containing heat-fusible fibers is preferably 10 g/m$^2$ to 175 g/m$^2$ and more preferably 17 g/m$^2$ to 85 g/m$^2$.

In step b, a fiber assembly containing latent crimpable fibers is transported from a container 14 to a carding machine 15 and opened by passing through the carding machine 15 to form a web 16 containing latent crimpable fibers. As a result of being opened by passing through the carding machine, the fibers can be made to be mainly oriented in the machine direction MD. The basis weight of the formed web 16 containing latent crimpable fibers is preferably 7 g/m$^2$ to 100 g/m$^2$ and more preferably 10 g/m$^2$ to 60 g/m$^2$. The step a and the step b can be carried out in any order.

In step c, the web 13 containing heat-fusible fibers and the web 16 containing latent crimpable fibers are superimposed to form a laminated web 18. Although an aspect is shown in FIG. 4 in which the formed web 16 containing latent crimpable fibers is superimposed on the web 13 containing heat-fusible fibers on the endless belt 17, the web 16 containing latent crimpable fibers is not necessarily required to be superimposed on the web 13 containing heat-fusible fibers, but rather the laminated web 18 may be formed by superimposing the web 13 containing heat-fusible fibers on the web 16 containing latent crimpable fibers. Namely, step a and step b may be carried out in any order, and when transporting the laminated web, the web 16 containing latent crimpable fibers may be on top or the web 13 containing heat-fusible fibers may be on top.

Step d is a step for generating a difference in shrinkage force in the laminated web in the machine direction MD as a result of the expression of crimping by the latent crimpable fibers during the heat treatment step. As a preferable method for achieving this, the laminated web is transported by placing on a support, in which liquid passage portions and protruding liquid blocking portions extending in parallel in the cross-machine direction CD alternately repeat in the machine direction MD, while spraying a liquid from a plurality of nozzles arranged in a row in the cross-machine direction to realign the fibers. Liquid is preferably sprayed from a plurality of nozzles arranged in a row in the cross-machine direction onto the side of the web containing latent crimpable fibers.

Figure 5:
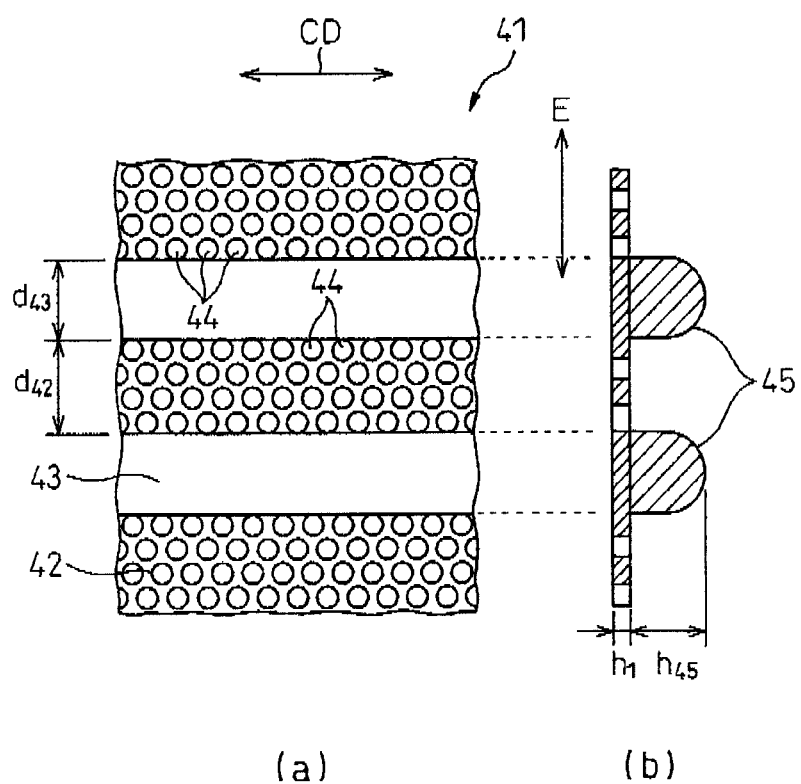
FIG. 5 is a drawing showing an example of a molding plate.

A support in which a molding plate is attached to the circumferential surface of a suction drum 19, for example, can be used for the support in which liquid passage portions and protruding liquid blocking portions extending in parallel in the cross-machine direction CD alternately repeat in the machine direction MD. FIG. 5 shows an example of a molding plate. FIG. 5($a$) is an overhead view of a molding plate 41, while FIG. 5($b$) is a cross-sectional view of the molding plate 41 taken along the circumferential direction E (machine direction MD). The molding plate 41 has liquid passage portions 42 and liquid blocking portions 43 alternately formed in the circumferential direction E of the suction drum 19, a plurality of holes 44 are formed in the liquid passage portions 42, and the holes 44 are connected to a suction mechanism (not shown) of the suction drum 19. Projections 45 are attached to the liquid blocking portions 43. In one example of the molding plate 41, the liquid passage portions 42 have a width $d_{42}$ in the circumferential direction E of 0.5 mm to 5 mm, extend over nearly the entire axial direction of the suction drum 19, namely the cross-machine direction CD, and a plurality of the holes 44 having a diameter of 0.2 mm to 1 mm are formed so as to form an aperture ratio of 15% to 30% with respect to the surface area of the liquid passage portions 42. The liquid blocking portions 43 have a width $d_{43}$ in the circumferential direction E of 0.5 mm to 5 mm, and extend over the entire axial direction of the suction drum 19. The width in the circumferential direction of those portions of the projections 45 that are fixed to the support is the width of the liquid blocking portions 43, and the projections 45 have a height $h_{45}$ of 0.5 mm to 10 mm. In addition, the cross-sectional shape of the projections 45 is preferably such that the cross-sectional area of a space formed by connecting the tops of adjacent projections 45 is larger than the cross-sectional area of the projections 45. Examples of such shapes include a circle, semi-circle, oval, trapezoid and triangle. As a result of adopting such a shape, the fiber web can be efficiently embedded between adjacent projections 45, thereby enabling the number of fibers within the protrusions to be increased and further strengthening the "arch structure" formed along the convex shape of the protrusions.

The peripheral velocity of the suction drum 19 to which the molding plate is attached is the same as the transport speed of the laminated web.

In a preferred aspect of step d, a liquid is sprayed onto the side of the web containing latent crimpable fibers from a plurality of nozzles arranged in a row in the cross-machine direction. In FIG. 4, reference symbol 19 indicates a suction drum that rotates in the machine direction MD, while reference symbol 20 indicates a plurality of nozzles arranged in a row in the cross-machine direction for spraying a liquid. The nozzles 20a are able to spray liquid towards the circumferential surface of the suction drum 19, and are separated from the circumferential surface of the suction 19 by a prescribed distance. The plurality of nozzles 20 are attached at required intervals to a pipe (not shown) extending in the axial direction of the suction drum 19, namely the cross-machine direction CD.

Although the plurality of nozzles 20 arranged in a row in the axial direction may consist of a single row as shown in FIG. 6(a), the nozzles are preferably composed by arranging in two or more rows from the viewpoint of fiber penetrability. For example, the nozzles may be composed of nozzle rows 21, 22 and 23 as shown in FIG. 6(b), and in a preferable example of an attached state thereof, the nozzles 20 are adjusted so as to be located along the same line in the machine direction MD in each of the nozzle rows 21, 22 and 23. In addition, the nozzle rows 21, 22 and 23 can be arranged while separated by intervals Q of 30° each in the circumferential direction of the suction drum 19 as shown in FIG. 7, and the nozzles 20 of each of the nozzle rows 21, 22 and 23 can be attached to a pipe at a pitch P of 5 mm in the cross-machine direction CD, for example. Liquid of a prescribed temperature can be sprayed at a required spray volume from the nozzle rows 21, 22 and 23. The liquid sprayed from the plurality of nozzles 20 is adjusted so as not to disturb the distribution state of the heat-fusible fibers of the first fibrous layer 4 of the web 18 as a result of mutual interference there between. In order to accomplish this, in the case, for example, the laminated web 18 having a total basis weight of 35 g/m² passes over the circumferential surface of the suction drum 19 having a diameter of 500 mm in 0.5 seconds, each of the nozzle rows 21, 22 and 23 are arranged at a pitch P of 5 mm in the cross-machine direction CD, and the distance of the nozzle rows 21, 22 and 23 from the circumferential surface of the suction drum 19 is adjusted to 5 mm to 8 mm, the laminated web preferably passes beneath the nozzles 20 after adjusting the thickness to about 2 mm to 5 mm with the suction of the suction drum 19. The aperture of the nozzles 20 used at this time is preferably about 0.5 mm to 1.5 mm, the spraying rate of liquid from the nozzles 20 is preferably 50 m/sec to 700 m/sec, and the suctioning rate of the suction drum 19 is preferably 2 m/sec to 7 m/sec.

The laminated web is then placed on the circumferential surface of the suction drum 19 to which the molding plate 41 is attached, and passes beneath the plurality of nozzles 20 arranged in a row in the cross-machine direction. Although a liquid is sprayed towards the laminated web from the nozzles 20, in the suction drum 19, the suction acts to suction the liquid.

Figure 8:
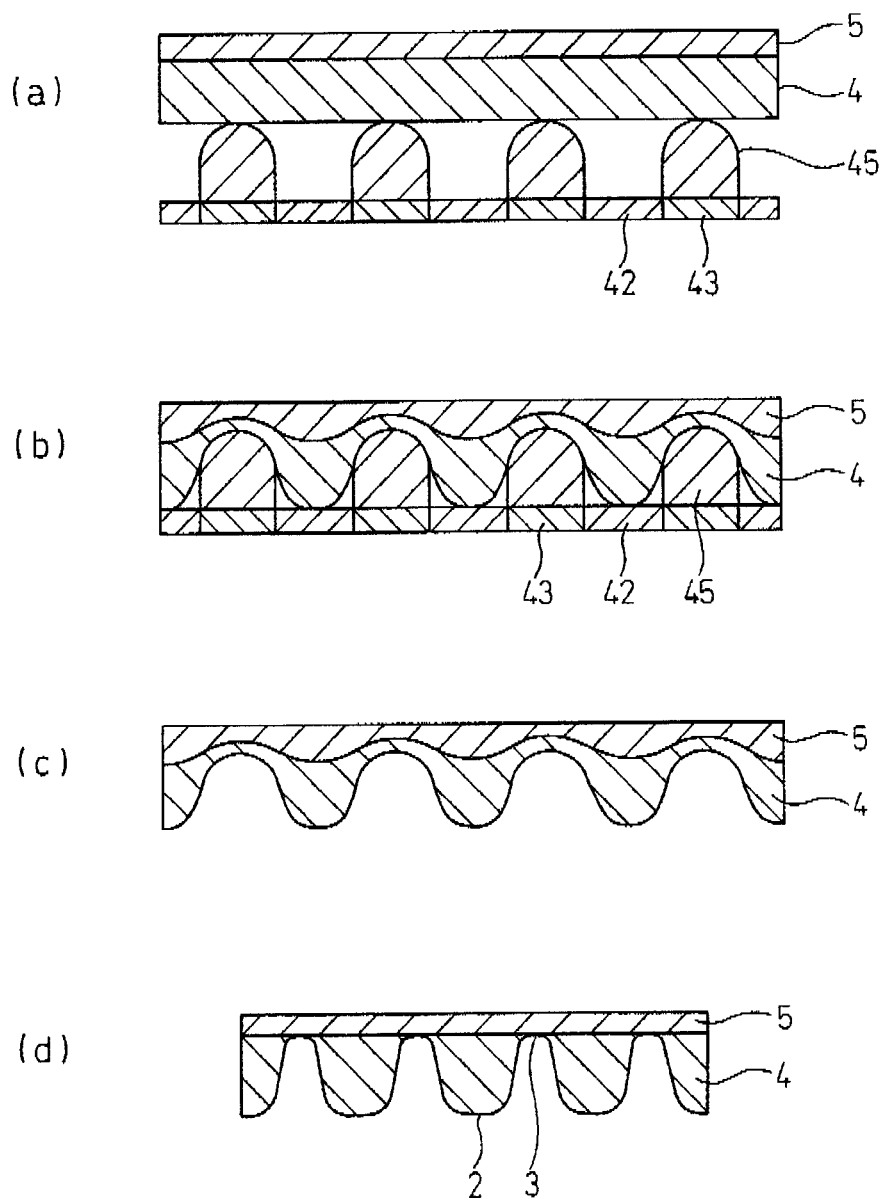
FIG. 8 is a schematic diagram for explaining a mechanism by which protrusions are formed.

FIG. 8 is a schematic drawing for explaining the mechanism by which the protrusions are formed. FIG. 8(a) shows a cross-sectional view in the machine direction of the laminated web after having entered step d but before being sprayed with liquid. FIG. 8(b) is a cross-sectional view in the machine direction of a region of the laminated web not sprayed with liquid after having been sprayed with liquid in step d. FIG. 8(c) is a cross-sectional view in the machine direction of a region of the laminated web not sprayed with liquid after going through step d. FIG. 8(d) is a cross-sectional view in the machine direction of a region of the web not sprayed with liquid after expression of crimping by the latent crimpable fibers in step f.

Figure 9:
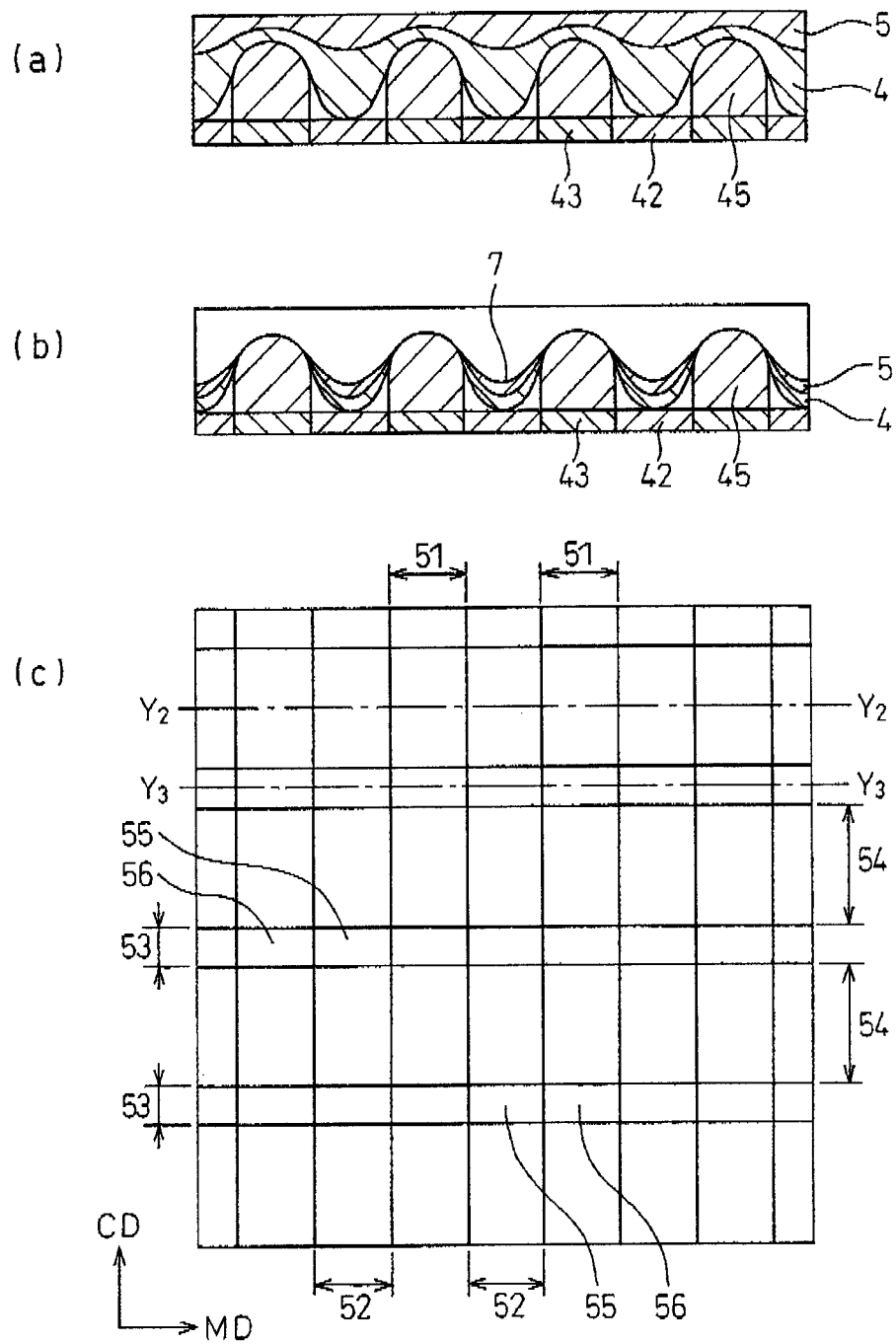
FIG. 9 is a drawing showing a state after a laminated web has been subjected to liquid spraying in step d.

FIG. 9 shows the state of the laminated web after having been sprayed with liquid in step d. FIG. 9(c) shows an overhead view, FIG. 9(a) shows a cross-sectional view taken along line $Y_2$-$Y_2$ of FIG. 9(c), and FIG. 9(b) shows a cross-sectional view taken along line $Y_3$-$Y_3$ of FIG. 9(c). In FIG. 9(c), reference symbols 51 indicate regions of the liquid blocking portions 43 (projections 45) of the molding plate 41, while reference symbols 52 indicate regions of the liquid passage portions 42 of the molding plate 41. Reference symbols 53 indicate regions sprayed with liquid, with reference symbols 54 indicates regions not sprayed with liquid.

In the laminated web sprayed with liquid, fibers directly below the nozzles 20 move in parallel in the cross-machine direction CD and accumulate in the regions 54 between adjacent nozzles 20 to form ridges. On the other hand, grooves are formed in the regions 53 directly below the nozzles 20.

The shape of the fiber web on the side of the molding plate 41 of the ridges 54 extending in the machine direction MD consists of repeating undulations in the machine direction MD (see FIG. 9(a)). In addition, bridges 7 connecting adjacent protrusions 2 are formed in regions 55 where the regions 52 of the liquid passage portions 42 of the molding plate 41 and the regions 53 sprayed with liquid intersect (see FIG. 9(c)). The bridges 7 are formed while the fiber web is embedded in the gaps between the projections 45 when liquid is sprayed from adjacent nozzles 20. At this time, fibers located on the side of the molding plate 41 of the ridges formed between the liquid spraying nozzles 20 are also embedded in the portions of the gaps between the projections 45, thereby resulting in a shape consisting of repeating undulations in the machine direction MD.

Moreover, at the projections 45 attached to the liquid blocking portions 43 of the molding plate 41 that form the circumferential surface of the suction drum 19, liquid that has been sprayed towards the laminated web 18 does not proceed to the inside of the suction drum 19, but rather flows in the cross-machine direction CD and machine direction MD along the surface of the projections 45. Due to this liquid, when fibers placed on the projections 45 are moved in the cross-machine direction CD and the machine direction MD, the through holes 6 are formed in regions 56 of the laminated web 18 where the regions 51 of the liquid blocking portions 43 (projections 45) and regions 53 sprayed with liquid intersect (see FIG. 9(c)).

In addition, when the majority of liquid sprayed towards fibers placed on the liquid passage portions 42 of the molding plate 41 proceed to the inside of the suction drum 19 through the holes 44 in the molding plate 41, a portion of the fibers remain directly below the nozzles 20 without moving in the cross-machine direction CD, and the bridges 7 that connect adjacent protrusions 2 are formed in the regions 55 where the regions 52 of the liquid passage portions 42 and the regions 53 sprayed with liquid intersect (see FIG. 9(c)). Since liquid is sprayed from adjacent nozzles 20, the bridges are formed while the fiber web is embedded in the portions of the gaps between the projections 45. At this time, due to the heat of the sprayed liquid, the heat-fusible fibers of the first fibrous layer directly beneath the liquid spraying nozzles 20 melt causing the heat-fusible fibers to be fixed.

The regions 51 of the web are portions in which through holes are present at fixed intervals in the cross-machine direction CD that do not contain elements that restrict shrinkage of the web in the machine direction MD as a result of expression of crimping by the latent crimpable fibers of the second fibrous layer, or in other words, are portions where shrinkage of the web occurs relatively easily. On the other hand, the regions 52 of the web are portions that are resistant to the occurrence of shrinkage of the web in the machine direction MD resulting expression of crimping by the latent crimpable fibers of the second fibrous layer due to the presence of bridges where the heat-fusible fibers of the first fibrous layer are melted and fixed at fixed intervals in the cross-machine direction CD, or in other words, are portions where shrinkage of the web occurs with relative difficulty.

Step e is a step for transporting a web 24 obtained in step d to step f. In step e, the web 24 is transported by being placed on an endless belt 25. The transport speed in step e is either the same as the transport speed in step d or is slight faster than the transport speed in step d. Step e is not necessarily required, and the web 24 in which fibers have been reoriented in step d may also be sent directly from step d to step f. However, step is preferably provided in order to stably transport the web 24.

Step f is a first heat, treatment step for expressing crimping of the latent crimpable fibers of the second fibrous layer.

The web obtained in step d is sent to the first heat treatment step f after going through the transport step 3 as necessary. In the first heat treatment step f, a first heat treatment dryer 26 is provided, the web 24 is placed on an endless belt 27, and the web 24 is passed through the first heat treatment dryer 26 to carry out heat treatment therein. In the first heat treatment step f, although the latent crimpable fibers of the second fibrous layer express crimping, heat treatment is carried out under temperature conditions within a range at which heat-fusible fibers of the first fibrous layer are not mutually fused and fixed, and the latent crimpable fibers of the second fibrous layer are made to express crimping.

Regions 52 where shrinkage of the web occurs with relative difficulty and regions 51 where shrinkage of the web occurs relatively easily are alternately present in the machine direction MD in the web obtained in step d. Accordingly, regions having varying degrees of shrinkage of the web caused by expression of crimping by the latent crimpable fibers of the second fibrous layer in the machine direction MD are present at prescribed intervals. During expression of crimping by the latent crimpable fibers of the second fibrous layer, the web shrinks from both the machine direction MD and the cross-machine direction CD using the regions 52 where web shrinkage occurs with relative difficulty as starting points, and a plurality of the protrusions 2 extending continuously in parallel in the cross-machine direction CD and a plurality of the recesses 3 extending in the cross-machine direction CD between adjacent protrusions 2 are formed.

Although FIG. 8(c) shows the state of the web after having gone through step d, in contrast thereto, in the web following expression of crimping by the latent crimpable fibers of the second fibrous layer 5 in step f as shown in FIG. 8(d), those portions of the web where shrinkage occurs relatively easily form the recesses 3 as a result of shrinking in the machine direction MD, and those portions of the web where shrinkage occurs with relative difficulty form the protrusions 2.

When the entire web shrinks in both the machine direction MD and the counter-machine direction CD due to expression of crimping by the latent crimpable fibers of the second fibrous layer, the heat-fusible fibers of the first fibrous layer do not adhere. Accordingly, since expression of crimping by the latent crimpable fibers of the second porous layer is not obstructed, the plurality of protrusions 2 continuously extending in parallel in the cross-machine direction CD are formed easily.

The temperature of the first heat treatment dryer 26 is within a range that does not exceed the fusing temperature of the heat-fusible fibers of the first fibrous layer, is preferably a temperature 0° C. to +50° C. higher, and more preferably a temperature +10° C. to +40° C. higher, than the temperature at which the latent crimpable fibers of the second fibrous layer express crimping. For example, in the case the temperature at which the latent crimpable fibers of the second fibrous layer express crimping is 80° C. and the melting point of the heat-fusible fibers of the first fibrous layer is 130° C., then the temperature of the first heat treatment dryer 26 is preferably 80° C. to 130° C. and more preferably 90° C. to 120° C.

Since the latent crimpable fibers of the second fibrous layer are mainly oriented in the machine direction MD, the direction of shrinkage of the latent crimpable fibers of the second fibrous layer is also mainly the machine direction MD.

In addition, since the plurality of protrusions 2 continuously extending in parallel in the cross-machine direction CD are formed easily, it is necessary for the second fibrous layer to aggressively shrink in the machine direction MD due to expression of crimping by the latent crimpable fibers of the second fibrous layer. Therefore, in the first heat treatment step f, means is used for lowering the resistance to crimping by the latent crimpable fibers. In other words, heat treatment is carried out in a state in which resistance to a force acting to cause shrinkage in the machine direction due to crimping by the latent crimpable fibers is small. Examples of means for lowering the resistance to expression of crimping by the latent crimpable fibers include a method in which the transport speed of the first heat treatment step f is made to be slower than the transport speed of the previous step, and a method that uses a floating dryer.

The previous step in the method in which the transport speed of the first heat treatment step f is made to be slower than the transport speed of the previous step refers to step e when step e is provided or step d when step e is not provided. If the transport speed of the first heat treatment step f is not made to be slower than the transport speed of the previous step, in the case tension has acted in the machine direction on the web 24 within the first heat treatment dryer 26, since shrinkage of the second fibrous layer resulting from expression of crimping by the latent crimpable fibers therein only occurs easily in the cross-machine direction CD where the degree of freedom is relatively high, adequate shrinkage in the machine direction MD cannot be imparted to the first fibrous layer and it becomes difficult to form the protrusions 2.

For example, the transport speed of the first heat treatment step f is preferably reduced to 50% to 90% of the transport speed of the previous step within a range such that adequate shrinkage is expressed in the machine direction MD and the sheet does not become warped or folded.

Figure 10:
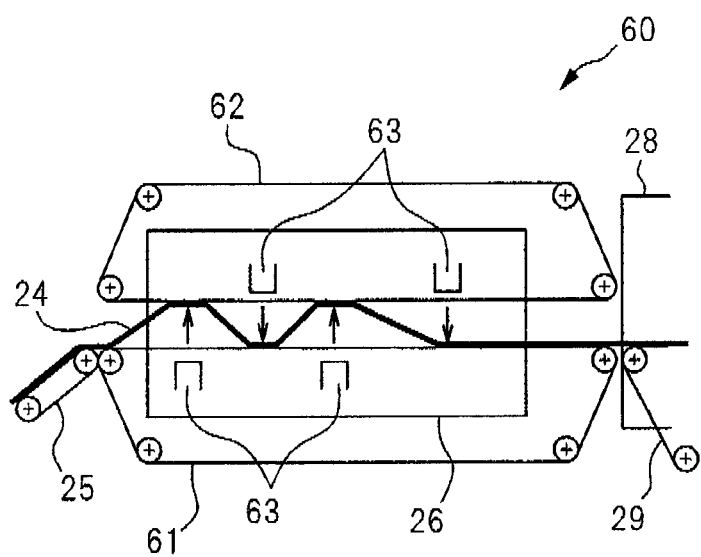
FIG. 10 shows an example of a floating dryer able to be used in a step f.

Although one component of resistance to shrinkage resulting from expression of crimping by the latent crimpable fibers is line tension during transport, another component is friction with the transport conveyor. In order to reduce this friction, a floating dryer 60 can be used as shown in FIG. 10. The floating dryer 60 has mesh conveyors 61 and 62 installed above and below while mutually separated, a plurality of hot air outlets 63 are provided to the inside of the mesh conveyors 61 and 62 (on the opposite side from the web 24), and heat treatment is carried out while blowing hot air towards one of the mesh conveyor 62 or 61 and moving the web 24 to the other mesh conveyor 62 or 61. As shown in FIG. 10, according to this preferable method for causing shrinkage in the machine direction MD, after having blown hot air from the lower mesh conveyor 61, hot air is then blown from the upper mesh conveyor 62, and as a result of alternatively blowing hot air from above and below, the web 24 is moved up and down, portions are formed that do not contact the mesh conveyors 61 and 62, and resistance to shrinkage due to expression of crimping by the latent crimpable fibers can be reduced. The floating dryer can be used in combination with a method for making the transport speed of the first treatment step slower than the transport speed of the previously step, and is preferably used in combination therewith.

Step g is a second heat treatment step for fusing the heat-fusible fibers of the first fibrous layer at those sites where the fibers mutually intersect. In the second heat treatment step g, a second heat treatment dryer 28 is provided, and the web in which the latent crimpable fibers have been crimped in step f is placed on an endless belt 29, and the belt is passed through the second heat treatment dryer 28 where it undergoes heat treatment therein. In the second heat treatment step g, heat treatment is carried out at a temperature equal to or higher than the fusing temperature of the heat-fusible fibers of the first fibrous layer, and as a result of the heat-fusible fibers fusing at those sites where the fibers mutually intersect, the protrusions of the first fibrous layer formed in steps d to f are fixed.

The temperature of the second heat treatment dryer 28 is preferably −10° C. to +40° C. higher and more preferably 0° C. to +20° C. higher than the melting point of the heat-fusible fibers of the first fibrous layer. For example, in the case the melting point of the heat-fusible fibers of the first fibrous layer is 130° C., then the temperature of the second heat treatment dryer 28 is preferably 120° C. to 170° C. and more preferably 130° C. to 150° C.

Step h is a step for cooling the web in which the heat-fusible fibers have been fused in step g. After having passed through the second heat treatment dryer 28 of step g, the web is transported by being placed on an endless belt 30 while cooling at room temperature. As a result of this cooling, fusion of the heat-fusible fibers of the first fibrous layer is fixed at those sites where the fibers mutually intersect and the first fibrous layer is fixed. The cooled web is then wound onto a roller 31.

EXAMPLES

Example 1

A non-woven fabric sheet was produced using the production device shown in FIG. 4.

In step a, polyester/polyethylene core-sheath type composite fibers (heat-fusible fibers, 2.6 dtex, fiber length: 51 mm, core:sheath weight ratio=50/50, melting point: 136° C.) were used as fibers for the first fibrous layer, and a web containing the heat-fusible fibers was formed having a basis weight of 20 g/m².

In step b, polypropylene/polyolefin-propylene copolymer latent crimpable, side-by-side composite fibers (2.6 dtex, fiber length: 51 mm, polypropylene:polyolefin-polypropylene copolymer weight ratio=50/50, area shrinkage rate: 80%, crimping expression temperature: 90° C.) were used as fibers for the second fibrous layer, and a web containing the latent crimpable fibers was formed having a basis weight of 15 g/m².

In step c, the web containing the latent crimpable fibers was laminated onto the web containing the heat-fusible fibers.

In step d, the web was sprayed at a flow rate of 214 m/sec using the molding plate shown in FIG. 5 (width $d_{42}$ in the circumferential direction of the liquid passage portions 42=2 mm, diameter of the holes 44 of the liquid passage portions 42=0.8 mm, aperture ratio of the holes 44 of the liquid passage portions 42=22%, width $d_{43}$ in the circumferential direction of the liquid blocking portions 43 (projections 45)=2 mm, height $h_{45}$ of the projections 45=2 mm, plate thickness $h_1$=0.3 mm), using two rows of nozzles having an aperture of 0.5 mm and pitch of 4 mm, making the distance from the suction drum 19 (distance from the tops of the projections 45) to be 5.0 mm, making the suctioning rate of the suction drum 19 to be 5 m/s, and using air at a temperature of about 140° C. for the sprayed liquid.

In step e, the transport speed was made to be 10 m/min.

In step f, the temperature of the first heat treatment dryer 26 was made to be about 110° C. at which the latent crimpable fibers express crimping and the heat-fusible fibers are not fused and fixed, the hot air blowing rate was made to be 0.7 m/s, and retention time in the first heat treatment dryer 26 was made to be 10 seconds. At this time, adequate shrinkage force was expressed in both the cross-machine direction CD and the machine direction MD and the transport speed was made to be 6 m/min (transport speed equal to 60% of the transport speed in step e) so as to prevent warping and folding of the sheet.

In step g, heat treatment was carried out at about 138° C. using a hot air blowing rate of 0.7 m/s and a retention time of 10 seconds, and heat-fusible fibers of the first fibrous layer were fused at those sites where the fibers mutually intersect.

In step h, the web was cooled at room temperature.

Figure 11:
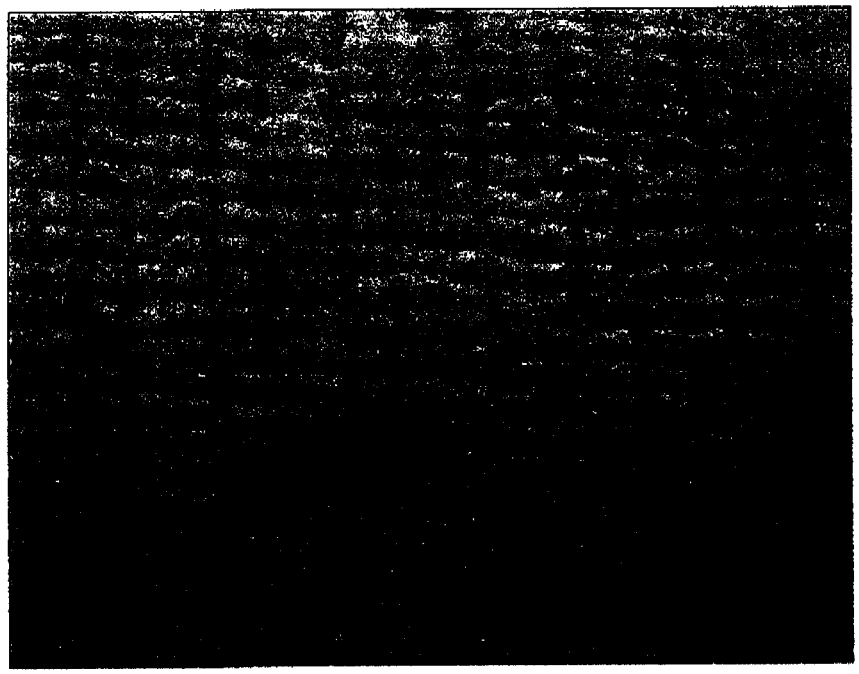
FIG. 11 is an overhead photograph (taken with a digital camera) of a non-woven fabric sheet obtained in Example 1.
Figure 12:
FIG. 12 is a micrograph (magnification factor: 30×) of a cross-section in the lengthwise direction of a protrusion of a non-woven fabric sheet obtained in Example 1.

After having gone through the aforementioned steps, a non-woven fabric sheet was obtained having a thickness of 1.99 mm, basis weight of 118 g/m², height difference D between the protrusions 2 and the recesses 3 of 1.70 mm, width of the protrusions 2 of 3.0 mm, and width of the recesses 3 of 1.0 mm. An overhead photograph of the resulting non-woven fabric sheet (as taken from the machine direction with a digital camera) is shown in FIG. 11, while a micrograph of a cross-section of a protrusion in the machine direction (magnification factor: 30×) is shown in FIG. 12.

Comparative Example 1

A non-woven fabric sheet was produced by making the following changes in comparison with Example 1.

In step c, a web containing heat-fusible fibers was superimposed on a web containing latent crimpable fibers.

A molding plate not having the projections 45 at the fluid passage portions 43 was used for the molding plate used in step d.

The transport speed in step f was made to be 90% of the transport speed of step e.

The non-woven fabric sheet was produced in the same manner as Example 1 with respect to the other steps.

Comparative Example 2

A non-woven fabric sheet was produced by making the following changes in comparison with Comparative Example 1.

Instead of using latent crimpable, side-by-side composite fibers, heat-fusible fibers identical to those used in the first fibrous layer were used as fibers for the second fibrous layer.

The transport speed in step f was made to be 100% of the transport speed of step e.

The non-woven fabric sheet was produced in the same manner as Comparative Example 1 with respect to the other steps.

The non-woven fabric sheets obtained in the example and comparative examples were evaluated for thickness, basis weight, thickness recovery rate after stretching in machine direction, permeation time after stretching in machine direction, KES compression workload WC and permeation time under load. The results are shown in Table 1. Furthermore, the methods used to evaluate these parameters are indicated below.

[Thickness]

A thickness gauge (Peacock, measuring surface: φ44 mm, measuring pressure: 3 g/cm²) was used to measure thickness. A piece of non-woven fabric sheet of a suitable size (larger than the probe) was placed between the measuring platform and the probe, and the probe was lowered from a fixed height to measure thickness. The average value of N=10 measurements was determined.

[Basis Weight]

The non-woven fabric sheet was cut to a size measuring 100 mm×150 mm, the piece of non-woven fabric sheet was weighed with an electronic balance followed by calculation of weight per square meter. The average of N=10 measurements was determined.

[Thickness Recovery Rate after Stretching in Machine Direction]

The procedure used to measure thickness (protrusion thickness $t_2$) recovery rate after stretching in the machine direction was as indicated below.

(1) The non-woven fabric sheet was cut to a size measuring 150 mm in the machine direction×50 mm in the cross-machine direction.

(2) The thickness of the cut sample was measured with the previously described thickness gauge.

(3) The non-woven fabric was then clamped and fixed in position at a chuck distance of 100 mm using the "Autograph AG-50NI" (Shimadzu System Solutions Co., Ltd.).

(4) Stretching distance was set corresponding to the ratio at which the non-woven fabric sheet was to be stretched followed by stretching the non-woven fabric sheet. For example, in the case of stretching 20%, the stretching distance is set to 120 mm.

(5) The non-woven fabric sheet was removed from the chuck followed by measuring thickness 1 minute later. Thickness was measured at a location near the center of the non-woven fabric sheet.

(6) Thickness recovery rate was calculated based on the following equation.

Thickness recovery rate (%)=Thickness after stretching/thickness before stretching×100

[Permeation Time after Stretching in Machine Direction]

(1) The surface sheet of a commercially available sanitary napkin (Unicharm Corp., Sofy Fuwatabi Slim, 25 cm) was removed, and a non-woven fabric sheet of the example or comparative examples was attached instead of the surface sheet to prepare a sample.

(2) The sample was placed on an acrylic plate having through holes and measuring 40 mm×10 mm, and a weight was placed on the acrylic plate to adjust the load on the sample to 2 gf/cm².

(3) 4 mL of artificial blood were dropped towards the sanitary napkin through the through holes in the acrylic plate at the rate of 90 ml/min. The artificial blood was prepared by mixing 80 g of glycerin, 8 g of sodium carboxymethyl cellulose (CMC), 10 g of NaCl, 4 g of NaHCO₃, 8 g of red dye no. 102, 2 g of red dye no, 2 and 2 g of yellow dye no. 5 in 100 cm³ of water and dissolving.

(4) The amount of time from the start of dropping of the artificial blood to migration of artificial blood accumulated in the through holes to the surface sheet was measured. The permeation time was used as an indicator of the quality of liquid permeability of the non-woven fabric.

[YES Compressive Workload WC]

KES compressive workload WC was measured with the "KES-F3 Compression Tester (Kato Tech Co., Ltd.), which is typically used as a device for measuring compression characteristics of sheet-like fiber products. Compressive workload WC (g·cm/cm²) indicates the compressive workload per unit area of a sample as determined by applying pressure to a measurement sample placed on a sample support stand from above at a constant rate of 0.02 mm/sec up to a compressive load of 50 g/cm³, and the smaller that value, the greater the resistance to compressive deformation.

[Permeation Time Under Load]

(1) The surface sheet of a commercially available sanitary napkin (Unicharm Corp., Sofy Fuwatabi Slim, 25 cm) was removed, and a non-woven fabric sheet of the example or comparative examples was attached instead of the surface sheet to prepare a sample.

(2) The sample was placed on an acrylic plate having through holes and measuring 40 mm×10 mm, and a weight was placed on the acrylic plate to adjust the load on the sample to 70 gf/cm².

(3) 4 mL of artificial blood were dropped towards the sanitary napkin through the through holes in the acrylic plate at the rate of 90 mL/min.

(4) The amount of time from the start of dropping of the artificial blood to migration of artificial blood accumulated in the through holes to the surface sheet was measured. The permeation time was used as an indicator of the quality of liquid permeability of the non-woven fabric under a load.

TABLE 1

|  | Example 1 | Comp. Ex. 1 | Comp. Ex. 2 |
|---|---|---|---|
| Upper layer fiber orientation | Perpendicular to protrusions | Parallel to protrusions | Parallel to protrusions |
| Lower layer fiber orientation | Perpendicular to protrusions | Parallel to protrusions | Parallel to protrusions |

TABLE 1-continued

|  |  |  | Example 1 | Comp. Ex. 1 | Comp. Ex. 2 |
|---|---|---|---|---|---|
| Sites adjacent to holes in CD direction present in recesses |  |  | Recesses | Protrusions | Protrusions |
| Fiber composition |  | Upper layer | Polyester/ polyethylene core-sheath composite fibers | Polyester/ polyethylene core-sheath composite fibers | Polyester/ polyethylene core-sheath composite fibers |
|  |  | Lower layer | Latent crimpable side-by-side composite fibers | Latent crimpable side-by-side composite fibers | Polyester/ polyethylene core-sheath composite fibers |
| Thickness | (mm) |  | 1.99 | 1.80 | 1.90 |
| Basis weight | (g/m$^2$) |  | 118 | 42 | 40 |
| Thickness recovery rate after stretching in MD direction | (%) | After 10% stretching | 98 | 97 | 87 |
|  |  | After 20% stretching | 90 | 83 | 73 |
| Permeation time after stretching in MD direction | (s) | No stretching | 4.43 | 4.45 | 4.63 |
|  |  | After 10% stretching | 4.60 | 4.75 | 5.77 |
|  |  | After 20% stretching | 4.62 | 5.23 | 6.24 |
| KES compressive workload | (gf · cm/cm$^2$) |  | 0.97 | 1.79 | 1.99 |
| Permeation time under load | (s) |  | 4.85 | 17.2 | 18.7 |

When the non-woven fabric sheets obtained in the example and comparative examples were compared for thickness after stretching by a prescribed percentage in the machine direction MD, the non-woven fabric sheets that used latent crimpable fibers in the second fibrous layer (Example 1 and Comparative Example 1) demonstrated higher thickness recovery rates than the non-woven fiber sheet not using latent crimpable fibers in the second fibrous layer (Comparative Example 2) since coiled, three-dimensional crimped fibers demonstrated a force that returns them to their original shape.

Moreover, the thickness recovery rate of Example 1 was higher than that of Comparative Example 1.

The reason for this is thought to be as follows. In Example 1, through holes are present at fixed intervals in a plurality of recesses extending in the cross-machine direction CD, and the protrusions 2 extend continuously in the cross-machine direction CD. Since through holes are present in the recesses 3, and the number of entangled fibers is lower in the recesses 3 in comparison with that of the protrusions 2, the strength thereof is relatively weaker than that of the protrusions. Accordingly, in the case a load has acted in the machine direction MD, since the plurality of recesses extending the cross-machine direction between adjacent protrusions are preferentially stretched rather than the plurality of protrusions continuously extending in parallel in the cross-machine direction CD, the convex shape of the protrusions is more resistant to deformation.

When artificial blood permeation times of the samples were measured after stretching, those samples having high thickness recovery rates before and after stretching were more resistant to changes in permeation time even after recovering from stretching.

On the basis of this result, Example 1 easily maintained the specific volume of the protrusions 2 and the gaps of the recesses 3 since there was little change in the convex shape of the protrusions 2 caused by stretching in the machine direction MD. Accordingly, even in cases of increased line tension resulting from increasing the non-woven fabric line speed, production can be carried out without causing deformation of the convex shape of the protrusions 2, and a non-woven fabric having a high excreted liquid permeation rate can be stably provided.

When the non-woven fabric sheets of the example and comparative examples were compared for KES compressive workload, the non-woven fabric sheet in which the fiber orientation of the first fibrous layer was perpendicular to the protrusions (Example 1) demonstrated a higher KES compressive workload than the non-woven fabric sheets in which the fiber orientation of the first fibrous layer was parallel to the protrusions (Comparative Examples 1 and 2).

The reason for this is thought to be as follows. The fibers of the first fibrous layer of Example 1 are oriented in a direction perpendicular to the plurality of protrusions extending in parallel in the cross-machine direction. Since the fibers are oriented in a direction perpendicular to the protrusions, the fibers within the protrusions easily adopt an "arch structure" that follows the convex shape of the protrusions. Accordingly, in the case compressive stress has acted in the direction of thickness of Example 1, the compressive stress acting on the protrusions is dispersed. Accordingly, since the protrusions have greater strength with respect to compression from the direction of thickness, the convex shape of the protrusions is resistant to deformation, and the specific volume of the protrusions and the gaps of the recesses can be maintained. As a result, permeation time when absorbing a liquid under a load can be shortened.

On the basis of this result, since the protrusions of Example 1 are resistant to crushing when force is applied in the direction of thickness, the specific volume of the protrusions and the gaps of the recesses can be maintained even in cases in which excessive body pressure is applied during use, thereby allowing body fluids to be temporarily retained.

Accordingly, in the case of using the non-woven fabric sheet of the present invention as a surface sheet of an absorbent article, since excreted liquid can be rapidly incorporated even in a state of being subjected to body pressure, leakage can be effectively prevented without allowing excreted liquid to spread out onto the skin of a user.

In addition, even in the case of using the non-woven fabric sheet of the present invention as an absorbent body of an absorbent article, since specific volume in the absorbent body is unlikely to be changed by body pressure, liquid that has passed through a surface sheet can be rapidly incorporated into the absorbent body, thereby effectively preventing leakage.

INDUSTRIAL APPLICABILITY

The non-woven fabric sheet of the present invention can be preferably used as a surface sheet or absorbent body of an absorbent article such as a disposable diaper or sanitary napkin.

BRIEF DESCRIPTION OF THE REFERENCE SYMBOLS

1 Non-woven fabric sheet
2 Protrusions
3 Recesses
4 First fibrous layer
5 Second fibrous layer
6 Through holes
7 Bridges
11 Container
12 Carding machine
13 Web
14 Container
15 Carding machine
16 Web
17 Endless belt
18 Laminated web
19 Suction drum
20 Nozzles
21,22,23 Nozzle rows
24 Web
25 Endless belt
26 First heat treatment dryer
27 Endless belt
28 Second heat treatment dryer
29 Endless belt
30 Endless belt
31 Roller
41 Molding plate
42 Liquid passage portions
43 Liquid blocking portions
44 Holes
45 Projections
60 Floating dryer
61,62 Mesh conveyors
63 Hot air outlets

The invention claimed is:

1. A method of processing a non-woven fabric sheet, comprising the steps of:
   a) opening a first fiber assembly containing heat-fusible fibers by passing the first fiber assembly through a carding machine to form a web containing heat-fusible fibers,
   b) opening a second fiber assembly containing latent crimpable fibers by passing the second fiber assembly through a carding machine to form a web containing latent crimpable fibers,
   c) superimposing the web containing heat-fusible fibers and the web containing latent crimpable fibers to form a laminated web,
   d) creating a difference in shrinkage force in the machine direction in the laminated web by causing crimping of the latent crimpable fibers during a heat treatment step over a prescribed width in the machine direction,
   f) heating the laminated web to a temperature that: i) is lower than the fusing temperature of the heat-fusible fibers; and ii) causes crimping of the latent crimpable fibers by lowering resistance to crimping of the latent crimpable fibers, and
   g) fusing the web obtained in step f at sites where the heat-fusible fibers mutually intersect by heating to a temperature equal to or higher than the fusing temperature of the heat-fusible fibers.

2. The method of processing a non-woven fabric sheet according to claim 1, wherein in step d the laminated web is transported by placing on a support having liquid passage portions and protruding liquid blocking portions extending in parallel in the cross-machine direction CD and alternately repeating in the machine direction MD, and fibers in the laminated web are reoriented by spraying a liquid from a plurality of nozzles arranged in the cross-machine direction.

3. The method of processing a non-woven fabric sheet according to claim 2, wherein in step f the lowering of resistance to crimping of the latent crimpable fibers is achieved by transporting the laminated web in step f at a lower transport speed than that of a previous step.

4. The method of processing a non-woven fabric sheet according to claim 3, wherein in step f the lowering of resistance to crimping of the latent crimpable fibers is achieved heat treating the laminated web in a floating dryer.

5. The method of processing a non-woven fabric sheet according to claim 3, further comprising the step of:
   e) transporting the web obtained in step d to step f between step d and step f.

6. The method of processing a non-woven fabric sheet according to claim 2, wherein in step f the lowering of resistance to crimping of the latent crimpable fibers is achieved heat treating the laminated web in a floating dryer.

7. The method of processing a non-woven fabric sheet according to claim 6, further comprising the step of:
   e) transporting the web obtained in step d to step f between step d and step f.

8. The method of processing a non-woven fabric sheet according to claim 2, further comprising the step of:
   e) transporting the web obtained in step d to step f between step d and step f.

9. The method of processing a non-woven fabric sheet according to claim 2, further comprising the step of:
   h) cooling the web obtained in step g after step g.

10. The method of processing a non-woven fabric sheet according to claim 1, wherein in step f the lowering of resistance to crimping of the latent crimpable fibers is achieved by transporting the laminated web in step f at a lower transport speed than that of a previous step.

11. The method of processing a non-woven fabric sheet according to claim 10, wherein in step f the lowering of resistance to crimping of the latent crimpable fibers is achieved heat treating the laminated web in a floating dryer.

12. The method of processing a non-woven fabric sheet according to claim 11, further comprising the step of:
   e) transporting the web obtained in step d to step f between step d and step f.

13. The method of processing a non-woven fabric sheet according to claim 10, further comprising the step of:
   e) transporting the web obtained in step d to step f between step d and step f.

14. The method of processing a non-woven fabric sheet according to claim 10, further comprising the step of:
   h) cooling the web obtained in step g after step g.

15. The method of processing a non-woven fabric sheet according to claim 1, wherein in step f the lowering of resistance to crimping of the latent crimpable fibers is achieved heat treating the laminated web in a floating dryer.

16. The method of processing a non-woven fabric sheet according to claim 15, further comprising the step of:

e) transporting the web obtained in step d to step f between step d and step f.

17. The method of processing a non-woven fabric sheet according to claim 15, further comprising the step of:
   h) cooling the web obtained in step g after step g.

18. The method of processing a non-woven fabric sheet according to claim 1, further comprising the step of:
   e) transporting the web obtained in step d to step f between step d and step f.

19. The method of processing a non-woven fabric sheet according to claim 18, further comprising the step of:
   h) cooling the web obtained in step g after step g.

20. The method of processing a non-woven fabric sheet according to claim 1, further comprising the step of:
   h) cooling the web obtained in step g after step g.

* * * * *